United States Patent [19]

Bye

[11] 4,340,502

[45] Jul. 20, 1982

[54] TRANSITION METAL COMPOSITION

[75] Inventor: Ashley D. Bye, The Hague, Netherlands

[73] Assignee: Imperial Chemical Industries Limited, London, England

[21] Appl. No.: 194,257

[22] Filed: Oct. 6, 1980

Related U.S. Application Data

[63] Continuation of Ser. No. 936,896, Aug. 25, 1978, abandoned.

[30] Foreign Application Priority Data

Aug. 31, 1977 [GB] United Kingdom ............... 36341/77
May 24, 1978 [GB] United Kingdom ............... 21732/78

[51] Int. Cl.$^3$ ................................................ C08F 4/64
[52] U.S. Cl. ................................ 252/429 B; 526/139
[58] Field of Search .................................... 252/429 B

[56]  References Cited

U.S. PATENT DOCUMENTS

| | | | |
|---|---|---|---|
| 3,117,834 | 1/1964 | Siggel et al. | 252/429 B X |
| 3,186,977 | 6/1965 | Coover et al. | 252/429 B X |
| 3,758,621 | 9/1973 | Morikawa et al. | 252/429 B X |
| 3,960,765 | 6/1976 | Shiga et al. | 252/429 B |
| 3,984,350 | 10/1976 | Karayannis et al. | 252/429 B |
| 3,992,320 | 11/1976 | Schneider et al. | 252/429 B |
| 4,007,133 | 2/1977 | Rust et al. | 252/429 B |
| 4,062,804 | 12/1977 | Ueno et al. | 252/429 B |
| 4,110,248 | 8/1978 | Sandis et al. | 252/429 B |
| 4,111,836 | 9/1978 | Karayannis et al. | 252/429 B |

FOREIGN PATENT DOCUMENTS

| | | |
|---|---|---|
| 2099150 | 2/1972 | France . |
| 2314924 | 1/1977 | France . |
| 2320308 | 3/1977 | France . |
| 52-91794 | 8/1977 | Japan . |
| 7608629 | 2/1977 | Netherlands . |
| 1324173 | 7/1973 | United Kingdom . |
| 1351822 | 5/1974 | United Kingdom . |
| 1359328 | 7/1974 | United Kingdom . |
| 1388308 | 3/1975 | United Kingdom . |
| 1391068 | 4/1975 | United Kingdom . |
| 1479651 | 7/1977 | United Kingdom . |
| 1482669 | 8/1977 | United Kingdom . |
| 1487393 | 9/1977 | United Kingdom . |
| 1503305 | 3/1978 | United Kingdom . |
| 1543868 | 4/1979 | United Kingdom . |
| 1558480 | 1/1980 | United Kingdom . |

Primary Examiner—Patrick Garvin
Attorney, Agent, or Firm—Cushman, Darby & Cushman

[57]  ABSTRACT

A transition metal composition has the formula:

$$TiCl_3(AlR_xX_{3-x})_nE_aL_b$$

where E is an ether or thioether; L is an organic phosphorus-containing Lewis Base; and a and b are each greater than 0.001 and not more than 0.50. The composition has a low surface area, typically less than 50 m$^2$/g. The composition can be prepared by reacting titanium tetrachloride with an organoaluminium compound, optionally heating the reaction product, contacting the reaction product at an elevated temperature with at least one of E and L and washing the product subsequent to the contacting with E. In the composition, E is conveniently di-n-butyl ether or di-isoamyl ether and L can be an organic phosphine, phosphine oxide, phosphite or phosphate. The composition can be used in a polymerization catalyst to polymerize or copolymerize olefine monomers. Copolymers having an advantageous combination of low temperature brittle point and Flexural Modulus are disclosed.

16 Claims, No Drawings

TRANSITION METAL COMPOSITION

This is a continuation, of application Ser. No. 936,896 filed Aug. 25, 1978 and now abandoned.

The present invention relates to transition metal compositions, the preparation of such compositions and the use of such compositions as a component of a catalyst system for the polymerisation of olefine monomers.

The polymerisation of olefine monomers using the so-called Ziegler-Natta catalysts has been known for a number of years. These catalysts comprise a compound of a transition metal together with an organic compound of a non-transition metal. There have been many proposals to improve the activity and/or stereospecificity of the catalyst system by the use of additional catalyst components or by modifying either the transition metal compound or the non-transition metal compound.

According to the present invention there is provided, as a new composition of matter, a product of the formula:

$$TiCl_3(AlR_xX_{3-x})_n E_a L_b$$

where
R is a hydrocarbyl group;
X is a halogen atom other than fluorine;
E is an ether or a thioether;
L is an organic phosphorus-containing Lewis Base compound;
x is such that $0 \leq x \leq 3.0$;
n is from 0 up to 0.5; and
a and b are each, independently, from 0.001 up to 0.50.

The group R is conveniently a hydrocarbyl group containing from 1 up to 20 carbon atoms and may be an alkyl, aryl, cycloalkyl, alkaryl or aralkyl group. Typically, the group R is an alkyl group containing from 2 up to 10 carbon atoms, for example an ethyl or butyl group.

Typically, X is chlorine and the value of x is such that $0 \leq x \leq 2.0$ is especially about one.

The value of n is preferably greater than 0 and less than 0.3, especially greater than 0 and less than 0.2.

The ether or thioether which is E is a monoether, polyether, monothioether or polythioether which is capable of forming coordination complexes or compounds with aluminium halides or aluminium alkyls, these complexes or compounds being soluble in at least one of the solvents selected from the monoether, polyether, monothioether and polythioether themselves, aromatic and aliphatic hydrocarbons and the halogen-containing derivatives thereof.

The ether or thioether which is E is a compound containing only ether or only thioether groups. The polyether and the polythioether contain at least two ether groups or at least two thioether groups respectively. The ether or thioether may be a compound of the type $R^1-Z-R^2$ where $R^1$ and $R^2$, which may be the same or different, are hydrocarbyl groups containing 1 up to 12 carbon atoms; and Z is an oxygen or a sulphur atom.

The groups $R^1$ and $R^2$ are conveniently the same and may be alkyl, aryl, alkaryl, aralkyl or cycloalkyl groups. It is preferred that $R^1$ and $R^2$ are phenyl groups or particularly alkyl groups containing from 4 up to 6 carbon atoms. Polyethers which may be used as the compound E include 1-methoxy-2-(β-methoxyethoxy)ethane and 1,2-diphenoxyethane. It is especially preferred that E is di-n-butyl ether or di-isoamyl ether. The compound L is a phosphorus-containing Lewis Base compound such as an organic phosphine or an organic phosphine oxide or a derivative thereof. Organic phosphorus-containing Lewis Base compounds which are suitable for use as components of olefine polymerisation catalysts, and which may be used as the compound L, are disclosed, inter alia, in British Patent Specifications Nos. 803,198; 920,118; 921,954; 1,017,977; 1,049,723; 1,122,010; 1,150,845; 1,208,815; 1,234,657; 1,324,173; 1,359,328; 1,383,207; 1,423,658; 1,423,659 and 1,423,660. The compound L is conveniently a compound of the general formula:

$$R^3 R^4 R^5 P(O)_m$$

where
$R^3$ is a hydrocarbyl, or a hydrocarbyloxy, group wherein the hydrocarbyl group contains up to 18 carbon atoms;
$R^4$ and $R^5$, which may be the same or different, are each a hydrogen atom or a group $R^3$; and
m is 0 or 1.

Preferably, $R^4$ and $R^5$ are hydrocarbyl, or hydrocarbyloxy, groups, for example as in tri-n-butyl phosphine, triphenyl phosphine, tri-n-butyl phosphine oxide, trioctyl phosphine oxide, triphenyl phosphine oxide, tributyl phosphite, triphenyl phosphite, tris(nonylphenyl)phosphite, triethyl phosphate, tributyl phosphate and triphenyl phosphate.

The value of a and b need not be the same and typically will be different. The value of a is conveniently from 0.01 up to 0.2 and the value of b is conveniently from 0.005 up to 0.20.

A particularly preferred composition of matter in accordance with the present invention has the formula:

$$TiCl_3(AlR^6_x Cl_{3-x})_n (R^7_2 O)_a L'_b$$

where
a, b, n and x are all as defined;
$R^6$ is an alkyl group having from 2 up to 10 carbon atoms;
$R^7$ is a phenyl group or an alkyl group having from 4 up to 6 carbon atoms; and
L' is tri-n-butyl phosphine, triphenyl phosphine, tri-n-butyl phosphine oxide, trioctyl phosphine oxide, triphenyl phosphine oxide, tributyl phosphite, triphenyl phosphite, tris(nonylphenyl)phosphite, triethyl phosphate, tributyl phosphate or triphenyl phosphate.

The composition of matter has a relatively low specific surface area. Thus, the specific surface area is typically less than 50 m²/g and especially from 1 up to 30 m²/g. The term "specific surface area" as used herein is the surface area of one gramme of the product, the surface area having been measured using the technique of BS 4359/1.

The colour of the composition of matter may be from violet to brown and the composition of matter is typically a reddish-brown in colour. The X-ray diffraction spectrum is typically that of the beta-form of titanium trichloride, but lines which are characteristic of the layer lattice forms (for example a line corresponding to a lattice spacing of about 5.9Å) have also been observed in the spectrum of some compositions of matter in accordance with the present invention.

As a further aspect of the present invention there is provided a process for the production of a titanium trichloride-containing composition which process comprises (1) reducing titanium tetrachloride by reacting the titanium tetrachloride with a reducing agent under conditions to give a titanium trichloride product which includes an associated aluminium compound containing aluminium and chlorine atoms, wherein the titanium trichloride is formed predominantly in the beta-form;

(2) contacting the reduction product with compound E and compound L either simultaneously or sequentially, at least part of the contacting being effected at a temperature of at least 60° C. in the presence of at least compound E or compound L; and (3) subsequent to the contacting with the compound E, washing the product obtained with an inert hydrocarbon or inert halohydrocarbon liquid.

The reduction product may be subjected to a thermal treatment at a temperature in the range from 40° C. up to 130° C. for a period of from 5 minutes up to 20 hours, and the thermally treated product may then be subjected to stage (2) of the process.

After step (3), the product may be subjected to an additional treatment in which an aluminium alkyl compound, typically diethyl aluminium chloride, is added, followed by an olefine monomer, typically propylene, conveniently in an amount of 0.1 up to 2.0 grammes for each gramme of the titanium trichloride-containing product.

The various stages of the preparation of the titanium trichloride-containing product are preferably effected in the presence of a suitable inert hydrocarbon liquid which is stirred. This hydrocarbon liquid is conveniently an aliphatic or cycloaliphatic hydrocarbon such as hexane, heptane, decane or dodecane or mixtures thereof.

Suitable reducing agents include organic aluminium compounds of the general formulae

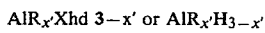
$AlR_{x'}Xhd\ 3-x'$ or $AlR_{x'}H_{3-x'}$ wherein

R and X are both as hereinbefore defined and $x'$ is such that $1.0 \leq x' \leq 3.0$; and it is preferred, when using such reducing agents, that the reduction is effected in the essential absence of aromatic hydrocarbons. An alternative reducing agent is a compound of the general formula

$TiCl_2.2AlCl_3$.arene where "arene" means a compound containing a six-membered hydrocarbon ring which ring contains a completely delocalised double bond system. The term "arene" includes benzene, toluene, xylene, durene and hexamethylbenzene and also compounds such as chlorobenzene. The compound $TiCl_2.2AlCl_3$.arene is soluble in aromatic liquids and thus reduction using this compound is effected either using a solution of the compound in an aromatic liquid or by grinding the solid compound in the presence of an excess of titanium tetrachloride.

If the reducing agent is an organic aluminium compound, it is conveniently one in which the value of $x'$ is from 1.5 up to 2.0. However, satisfactory products may be obtained when $x'$ has a value of 3.0. The organic aluminium compound may be aluminium triethyl or more preferably diethyl aluminium chloride or ethyl aluminium sesquichloride.

The reduction of the titanium tetrachloride is preferably carried out at a temperature which is below about 80° C. The temperature used depends on the particular reducing agent which is used. Thus, if the reducing agent is an alkyl aluminium sesquihalide, it is preferred to carry out the reduction at a temperature of between −20° C. and +20° C., very conveniently at 0° C. If the reducing agent is a dialkyl aluminium halide, whilst the temperature may be lower, for example as low as −40° C., satisfactory products can be obtained by using temperatures in the same range, that is temperatures in the range from −20° C. up to +20° C., although temperatures of −40° C. up to +10° C. are particularly suitable. If the reducing agent is an aluminium trialkyl, or an organic aluminium hydride, then lower reduction temperatures are preferred, particularly temperatures from −100° C. up to 0° C., especially about −70° C. up to about −40° C. If the reducing agent is an alkyl aluminium dihalide the preferred reduction temperatures are in the range from 0° C. up to 40° C., especially from 10° C. up to 30° C. Using the compound $TiCl_2.2AlCl_3$.arene as the reducing agent, the reduction may be effected at a temperature of from −80° C. up to +80° C., conveniently in the range from 0° C. up to 40° C.

The quantity of the reducing agent depends on the particular reducing agent which is used. Using an organic aluminium compound the proportion used is typically from 0.1 up to 2.0 moles of the organic aluminium compound for each mole of titanium tetrachloride. Using a dialkyl aluminium halide, or a material such as an aluminium sesquihalide which may be regarded as containing a proportion of a dialkyl aluminium halide, the preferred proportions of the organic aluminium compound are from 0.5 up to 1.5 moles of dialkyl aluminium halide for each mole of titanium tetrachloride. Using an aluminium trialkyl the preferred proportions are less and are typically in the range from 0.25 up to 0.5 moles for every mole of titanium tetrachloride. Using a compound of the type $TiCl_2.2AlCl_3$.arene, it is preferred to use equimolar proportions of the two reactants or an excess quantity of titanium tetrachloride.

The titanium trichloride-containing product obtained in stage (1) of the process is a solid which may be separated from the reaction medium and washed several times and finally resuspended in a sample of fresh hydrocarbon liquid. However, it is preferred that stage (2) or the optional thermal treatment stage, is effected in the presence of the liquid reaction medium from stage (1) when the reducing agent is an organic aluminium compound.

In the optional thermal treatment stage, the reduction product is preferably heated to a temperature of at least 60° C. The time of heating is dependent on the temperature used and shorter times are preferably used at higher temperatures. It is preferred that the conditions of the temperature and time are such that the heated product contains a small proportion of the layer lattice structure as shown by the X-ray diffraction pattern of this material.

If the optional thermal treatment stage is effected, it is preferred that the heated product is separated from the reaction medium and washed several times before effecting stage (2).

The compounds E and L may be added simultaneously or sequentially and, in the latter case, the compounds E and L may be added in either order. It is preferred that the compound E and the compound L are added separately and particularly useful results have been obtained when the compound E has been added first.

The contacting of the reduction product with the compounds E and L may be effected by adding one, or both, of the compounds to a stirred suspension of the reduction product at ambient temperature and then heating the mixture to the temperature of at least 60° C. However, it is preferred to heat the reduction product to the temperature of at least 60° C. and then add one, or both, of the compounds E and L to the heated material. It is not necessary to contact the reduction product at a temperature of at least 60° C. with both compound E and compound L, since satisfactory results have been obtained by contacting the reduction product with only one of compound E or compound L at the temperature of at least 60° C. and thereafter contacting the reduction product with the other compound at a temperature below 60° C. such as ambient temperature. It is however preferred to heat the reduction product, which may have been subjected to the optional thermal treatment, to the temperature of at least 60° C., and, whilst maintaining that temperature, add first the compound E and thereafter the compound L.

If desired the contacting with compound E or compound L may be repeated and using such a procedure the reduction product is preferably separated from the reaction mixture and washed before repeating the contacting with compound E or compound L.

Contacting with compounds E and L may be effected in more than one step, for example by repeating the contacting with at least one of the compounds E or L. Alternatively, a first contacting step may be effected with one of the compounds E and L, and a further and separate contacting step is then effected with the other one of compounds E and L. If contacting is effected in more than one step, it may be sufficient to wash the product between the contacting steps and washing after the final contacting step may not be necessary. However it will be appreciated that such a procedure is possible only if washing is effected after contacting with compound E and thereafter the final contacting step is effected without the addition of any of the compound E. A convenient technique for effecting such a procedure is to heat the product of stage (1) to the temperature of at least 60° C., add compound E to the heated product some time after the desired temperature has been attained, for example 30 minutes to two hours after attaining the desired temperature, wash the heated product, heat the washed product to the temperature of at least 60° C. and add compound L at any time after attaining the desired temperature.

If stage (2), the contacting with compounds E and L, is effected in a single step, then the final stage of the process is to wash the product of stage (2). However, it is not necessary to subject the titanium trichloride product to a final washing stage provided that the titanium trichloride product is not contacted with compound E after the final washing stage.

Although washing can be effected at various stages of the process, the only necessary washing stage is subsequent to the contacting, or the final contacting, with the compound E.

The amount of the compound E which is used is preferably from 0.5 up to 3.0 moles for every mole of titanium trichloride present in the reduction product and it is particularly preferred to use between 0.8 and 2.5 moles per mole of titanium trichloride present in the reduction product.

The amount of the compound L which is used is conveniently in the range from 0.01 up to 2.0 moles for each mole of titanium trichloride present in the reduction product. It is particularly preferred to use from 0.01 up to 0.5 mole of the compound L, especially from 0.02 up to 0.2 mole of the compound L.

It will be appreciated that the optimum proportions of the compounds L and E will be dependent on the particular compounds used, but these optimum proportions can be determined readily by experiment.

The temperature at which the contacting of the reduction product with the compound E and/or the compound L is effected is at least 60° C. and may be up to 150° C. It is preferred to use temperatures of at least 80° C. and not more than 130° C. Especially preferred temperatures are in the range from 90° C. up to 120° C. The heating time is preferably at least one hour and conveniently does not exceed 20 hours, particularly at least 2 hours and not more than 10 hours.

If compounds E and L are added to the reduction product at the temperature of at least 60° C., and the reduction product has been subjected to optional thermal treatment stage, it is preferred that at least one of the compounds E or L is added as soon as the reduction product attains the desired temperature. If compounds E and L are added separately in a single step, the second of the two compounds is conveniently added 5 minutes to two hours, for example 30 minutes, after the addition of the first of the two compounds.

The new composition of matter of the present invention may be used as one component of an olefine polymerisation catalyst.

Thus, according to a further aspect of the present invention there is provided an olefine polymerisation catalyst comprising: (1) a titanium trichloride-containing material of the type hereinbefore described; and (2) at least one organo-metallic compound of aluminium, or of a non-transition metal of Group IIA of the Periodic Table, or a complex of an organo-metallic compound of a non-transition metal of Group IA or Group IIA of the Periodic Table with an organo-aluminium compound.

The organo-metallic component which is component (2) of the catalyst can be a Grignard reagent which is substantially ether-free or a compound such as diphenyl magnesium. Alternatively, this component can be a complex of an organo-metallic compound of a non-transition metal of Groups IA or IIA with an organo-aluminium compound, for example Mg[Al(C$_2$H$_5$)$_4$]$_2$ or lithium aluminium tetraalkyl. It is preferred that component (2) is an organo-aluminium compound such as a hydrocarbyl aluminium sulphate, a hydrocarbyl oxyhydrocarbyl aluminium, or particularly a trihydrocarbyl aluminium or dihydrocarbyl aluminium halide or hydride, especially triethylaluminium or diethylaluminium chloride since catalysts including triethylaluminium give a high polymerisation rate whilst catalysts including diethylaluminium chloride give a relatively high percentage yield of the desirable insoluble (isotactic) polymer. A mixture of compounds can be used if desired, for example, a mixture of trialkyl aluminium and a dialkyl aluminium halide. It may be preferred to use catalysts giving a low level of residual halogen in the polymer product in which case the organo-metallic component is desirably a halogen-free compound particularly a trihydrocarbyl aluminium.

The catalyst can also contain, in addition to components (1) and (2), a further component, component (3), which is an organo-Lewis Base compound. This can be any Lewis Base which is effective to alter the activity and/or stereospecificity of a Ziegler catalyst system. A wide range of Lewis Bases have such an effect and these include compounds containing phosphorus and/or nitrogen atoms, oxygen compounds such as ethers, esters, ketones, and alcohols, and their sulphur-containing analogues, silicon compounds such as silanes and siloxanes, sulphones, sulphonamides and fused-ring heterocyclic sulphur compounds. Catalysts containing organo-Lewis Base compounds, or complexes including organo-Lewis Base compounds, are disclosed, inter alia, in British Patent Specifications Nos. 803,198; 809,717; 880,998; 896,509; 920,118; 921,954; 933,236; 940,125; 966,025; 969,074; 971,248; 1,013,363; 1,017,977; 1,049,923; 1,122,010; 1,150,845; 1,208,815; 1,234,657; 1,324,173; 1,359,328; 1,383,207; 1,423,658; 1,423,659 and 1,423,660; Belgian Patent Specification No. 693,551; and published German Patent Application Nos. 2 600 552. It is preferred to use, as the organo-Lewis Base compound, a Lewis Base which contains at least one atom of sulphur, nitrogen and/or phosphorus. Thus preferred organo-Lewis Base compounds, which can be used as the optical component (3) of the catalyst, include sulphur compounds such as diphenylsulphone, secondary or tertiary amines such as dibutylamine or tributylamine, diamines such as N,N,N',N'-tetramethylethylenediamine, and compounds which include both phosphorus and nitrogen atoms, such as hexamethylphosphoric triamide; N,N,N',N'-tetramethylethyl phosphorodiamidate; N,N,N',N',N"-pentamethyl-N"-β-dimethylaminoethylphosphoric triamide; 2-dimethylamino-1,3-dimethyl-1,3,2-diaza-phospholidine-2-oxide and octamethylpyrophosphoramide.

In addition to, or instead of, the organo-Lewis Base compound which is component (3), the catalyst may also include a substituted or unsubstituted polyene (component (4)), which may be an acyclic polyene such as 3-methyl-heptatriene (1,4,6) or a cyclic polyene such as cyclooctatriene, cyclooctatetraene or cycloheptatriene or derivatives of the cyclic polyenes such as the alkyl- or alkoxy-substituted cyclic polyenes; tropylium salts or complexes, tropolone or tropone.

The proportions of the various catalyst components can be varied widely depending both on the materials used and the absolute concentrations of the components. Typically for each gramme atom of the transition metal which is present in component (1) of the catalyst, there is present at least 0.05, and preferably at least 1.0, and if desired as many as 50 or even more, moles of component (2). In general it is preferred to use not more than 25 moles of the organo-metallic component for each mole of the transition metal catalyst compound present in component (1). If a Lewis Base is included, then for each mole of the transition metal compound there is conveniently present from 0.01 up to 10, preferably from 0.1 up to 4, moles of the Lewis Base, provided that the amount of Lewis Base is less than the amount of component (2). Any polyene which is present, plus any Lewis Base, should preferably, in total number of moles, be less than the number of moles of component (2). For each mole of component (2) the number of moles of polyene is conveniently in the range 0.01 up to 1.0, especially 0.05 up to 0.5, for example from 0.1 up to 0.2. If both Lewis Base and polyene are included, these can conveniently be used in equimolar proportions but the relative proportions of these components may be varied to give the optimum results.

The catalysts of the present invention are particularly suitable for the polymerisation and copolymerisation of olefine monomers by contacting at least one olefine monomer with a catalyst of the type hereinbefore defined.

More specifically, there is provided a process for the production of a polymer or copolymer of an olefine monomer wherein at least one olefine monomer, or a mixture of at least one olefine monomer and ethylene, is polymerised by contacting the at least one olefine, or mixture thereof with ethylene, under polymerisation conditions with an olefine polymerisation catalyst as hereinbefore defined.

Monomers which can be polymerised by the present process include butene-1, and 4-methylpentene-1 and particularly propylene. These olefines may be copolymerised together or preferably may be copolymerised with ethylene, conveniently using a sequential polymerisation process such as is described in British Patents Nos. 970,478; 970,479 and 1,014,944.

Surprisingly, although component (1) of the catalyst system contains some titanium trichloride in the beta-form, it has beem found that the process of the present invention can be used for the polymerisation of propylene to give a relatively low proportion of the undesirable soluble polymer. Furthermore, many of the catalyst systems give a high rate of polymerisation.

It is preferred to effect polymerisation using monomers (and diluents when used) which have a high degree of purity, for example a monomer containing less than 5 ppm by weight of water and less than 1 ppm by weight of oxygen. Materials having a high degree of purity can be obtained by processes such as those described in British Patent Specifications Nos. 1,111,493, 1,226,659 and 1,383,611.

Polymerisation can be carried out in the known manner, for example in the presence or absence of an inert diluent such as a suitably purified paraffinic hydrocarbon, in the liquid phase using excess liquid monomer or in the gaseous phase.

If polymerisation is effected in the gaseous phase, it may be effected by introducing the monomer, for example propylene, into the polymerisation vessel as a liquid and operating with conditions of temperature and pressure within the polymerisation vessel which are such that the liquid monomer vaporises, thereby giving an evaporative cooling effect, and essentially all of the polymerisation occurs with the monomer in the gaseous phase. Polymerisation in the gas phase is preferably effected using conditions which are such that the monomer is at a temperature and partial pressure which are close to the dew point temperature and pressure for that monomer. Such a procedure is described in more detail in published German Patent Application No. 2,616,356. Polymerisation in the gaseous phase can be effected using any technique suitable for effecting a gas solid reaction such as a fluidised bed reactor system, a stirred bed reactor system or a ribbon blender type of reactor.

Polymerisation may be effected either in a batch manner or on a continuous basis and the catalyst components may be introduced into the polymerisation vessel separately or all the catalyst components may be mixed together before being introduced into the polymerisation reactor.

The polymerisation can be effected in the presence of a chain transfer agent such as hydrogen or a zinc dialkyl, in order to control the molecular weight of the product formed. If hydrogen is used as the chain transfer agent, is is conveniently used in an amount of from 0.01 up to 5.0%, particularly from 0.05 up to 2.0% molar relative to the monomer. The amount of chain transfer agent will be dependent on the polymerisation conditions, especially the temperature, which is typically in the range from 20° C. up to 100° C., preferably from 50° C. up to 85° C.

Using catalysts in accordance with the present invention propylene may be polymerised to give a polymer having a high flexural modulus, for example at least 1.00 GN/m$^2$, particularly at least 1.30 GN/m$^2$ and especially up to 1.70 GN/m$^2$.

Particularly useful copolymers can be obtained using catalysts in accordance with the present invention.

Thus, as a further aspect of the present invention there is provided a copolymer of propylene and ethylene comprising a sequence of homopolymerised propylene and a sequence of propylene copolymerised with ethylene, said copolymer having a low temperature brittle point of −20° C. or lower and a flexural modulus of at least 1.35 GN/m$^2$.

The flexural modulus is determined in the manner as set out in Note (h) to Table 5 hereafter and the low temperature brittle point is determined in the manner set out in Note (k) to Table 6 hereafter. The flexural modulus may be as high as 1.50 GN/m$^2$ and preferred copolymers in accordance with the present invention have a flexural modulus of at least 1.40 GN/m$^2$. The low temperature brittle point may be as low as −35° C. and is preferably −25° C. or lower. Particularly preferred copolymers have a low temperature brittle point of −25° C. or lower and a flexural modulus of at least 1.40 GN/m$^2$.

As yet a further aspect of the present invention there is provided a copolymer of propylene and ethylene comprising a sequence of homopolymerised propylene and a sequence of propylene copolymerised with ethylene, said copolymer having a low temperature brittle point of −40° C. or lower and a flexural modulus of at least 1.20 GN/m$^2$.

The low temperature brittle point of such copolymers is typically in the range −40° C. to −50° C. and the flexural modulus may be as high as 1.30 GN/m$^2$.

Polymers produced by the process of the present invention have a high molecular weight as indicated by the melt flow index measured according to ASTM Test Method D 1238-70, using Condition N (that is a temperature of 190° C. and a weight of 10 kgm). Polymers obtained in accordance with the present invention have a melt flow index of less than 200 and preferred polymers have a melt flow index of less than 100, particularly less than 50, for example between 5 and 50.

Various aspects of the present invention will now be described with reference to the following Examples which are illustrative of the invention. In the Examples, all operations were effected under an atmosphere of nitrogen unless otherwise indicated.

EXAMPLE 1

(A) Reduction of titanium tetrachloride

A solution of 4.21 moles of titanium tetrachloride in 2.2 liters of pure n-heptane was placed in a five litre nitrogen-purged dry jacketed glass reaction vessel. The solution was cooled to a temperature in the range 8° C. to 10° C. and stirred at 250 rpm. A solution of ethyl aluminium sesquichloride in n-heptane (containing 500 grammes of the sesquichloride for each liter of n-heptane) was added to the contents of the reaction vessel over a period of 90 minutes. The quantity added was sufficient to provide 2.868 moles of the ethyl aluminium sesquichloride (this contained 2.868 moles of diethyl aluminium chloride). The temperature was maintained at 8° C. to 10° C. throughout the addition and the mixture was stirred. At the end of the addition of the sesquichloride solution, the mixture was stirred for a further 4 hours whilst maintaining the temperature of 8° C. to 10° C.

The whole mixture was then heated up to a temperature of 90° C. whilst still stirring. The temperature was maintained at 90° C. for 90 minutes, the mixture was allowed to cool and settle, the supernatant liquid was decanted off and the residual solid was then washed 5 times using 2 liters of purified n-heptane for each wash. The washed product was then suspended in 2.5 liters of heptane and the suspension obtained was then split up into several portions.

(B) Treatment with di-n-butyl ether

A portion equivalent to one fifth of the suspension obtained by the foregoing procedure was then treated with neat di-n-butyl ether in the following manner. A sufficient quantity of the di-n-butyl ether was added to provide 1.1 mole of the ether for each mole of titanium trichloride present in the suspension, which was being stirred. The addition was effected at room temperature and the product was then heated up to 90° C. which temperature was maintained for 1 hour.

(C) Treatment with tributyl phosphine

To the stirred suspension from (B), which was being maintained at 90° C., tributyl phosphine was added (neat) in a quantity sufficient to provide 0.084 moles of tributyl phosphine for each mole of titanium trichloride present. The temperature of 90° C. was maintained for a further one hour with stirring. The mixture was then allowed to cool to room temperature and the solid was allowed to settle. The supernatant liquid was decanted off and the solid was then washed 5 times with n-heptane using 500 ml of n-heptane for each wash. A sample of the product was dried and subjected to surface area measurements and to analysis. The remainder of the product was suspended in 500 ml of n-heptane.

COMPARATIVE EXAMPLE A

Treatment with di-n-butyl ether only

The heat treatment in the presence of di-n-butyl ether described in Example 1 was repeated except that the reaction mixture was maintained at 90° C. for a time of 2 hours. This heated product was then allowed to cool and was washed 5 times with n-heptane and finally resuspended in n-heptane. The washing procedure was also as described in Example 1.

EXAMPLE 2

A quantity of n-heptane supplied by British Drug Houses and conforming to the Institute of Petroleum specification was passed, at room temperature, through a column containing BTS catalyst and a molecular sieve. After this treatment, the only impurity which could be detected was toluene at a level of about 0.01% by volume. This will be referred to as "purified n-heptane".

A further quantity of n-heptane was purged with nitrogen at ambient temperature for one hour. This will be referred to as "purged n-heptane".

The reduction stage was as described in Example (1A) and used the purified n-heptane.

The treatment with di-n-butyl ether was effected on a one sixth portion of the product from stage (A), the ether being added in an amount of 1.1 moles of ether for each mole of titanium trichloride present and the addition being made when the suspension had attained a temperature of 90° C. After one hour at 90° C., 0.84 moles of tributyl phosphine were added for each mole of titanium trichloride present in the product from stage (A), and heating at 90° C. was continued for a further hour.

The product obtained was allowed to cool and was washed as in Example 1. All stages of the preparation, other than the last three washes, were effected using purified n-heptane. The last three washes were effected using purged n-heptane and the product was suspended in purged n-heptane.

During this preparation the suspension could be handled easily and there were no problems of agglomeration of the solid particles. In the process of Example 1 there were agglomeration problems and these problems were reduced only when the temperature of 90° C. was attained.

The product of this Example had a superior particle form compared to the product of Example 1, and could be handled more readily than the product of Example 1.

EXAMPLE 3

The procedure of Example 2 was repeated except that the quantity of tributyl phosphine was 0.028 moles for each mole of titanium trichloride.

EXAMPLE 4

The procedure of Example 2 was repeated except that the quantity of tributyl phosphine was 0.14 moles for each mole of titanium trichloride.

EXAMPLES 5 TO 7

The procedure of Example 2 was repeated except that the treatment with di-n-butyl ether, and the subsequent addition of tributyl phosphine, were effected at temperatures other than 90° C. Additionally subsequent to the heating of the reduction product all the washing and heating steps were effected in a mixed aliphatic hydrocarbon consisting predominantly of $C_{12}$ isomers.

The temperatures of the treatments with the ether and phosphine are set out in Table 1.

TABLE 1

| Example No. | Temperature of contacting with ether and phosphine (°C.) |
|---|---|
| 5 | 80 |
| 6 | 100 |
| 7 | 120 |

COMPARATIVE EXAMPLE B

Treatment with di-n-butyl ether

The reduced and heat-treated solid used in the preparation of the products of Examples 5 to 7 was heated to 90° C. and 1.1 moles of di-n-butyl ether was added for each mole of titanium trichloride and the temperature maintained at 90° C. for two hours and the product obtained was washed 5 times. Subsequent to the heating of the reduction product, all stages were effected using the same aliphatic hydrocarbon as was used in Examples 5 to 7.

EXAMPLE 8

The procedure of Example 2 was repeated except that di-n-butyl ether and tributyl phosphine were mixed together and the mixture formed was added to the reduction product when it attained a temperature of 90° C. The temperature of 90° C. was maintained for two hours.

EXAMPLE 9

The procedure of Example 2 was repeated except that the tributyl phosphine was added first, when the temperature attained 90° C., and the di-n-butyl ether was added after the mixture had been at 90° C. for one hour.

EXAMPLE 10

The procedure of Example 2 was repeated except that only di-n-butyl ether was added to the reduction product at 90° C., the temperature was maintained for two hours, the mixture was allowed to cool to ambient temperature (about 20° C.), and then the tributyl phosphine was added. The solid was contacted with the tributyl phosphine at ambient temperature for 30 minutes and was then washed as in Example 2.

EXAMPLES 11 TO 13

The procedure of Example 2 was repeated except that the thermal treatment of the reduced solid was either omitted or varied. Details of the thermal treatment are set out in Table 2.

TABLE 2

| Example No. | Thermal Treatment | |
|---|---|---|
| | Time (hours) | Temperature (°C.) |
| 11 | NIL | — |
| 12 | 1.5 | 70 |
| 13 | 1.5 | 106 |

EXAMPLES 14 AND 15

The procedure of Example 2 was repeated except that different proportions of di-n-butyl ether were used, as set out in Table 3.

TABLE 3

| Example No. | Quantity of di-n-butyl ether (mole/mole of $TiCl_3$) |
|---|---|
| 14 | 0.5 |
| 15 | 2.0 |

The products of Examples 1 to 7 and 11 to 15 were subjected to chemical analysis and measurement of surface area. The X-ray spectrum was obtained for some of the products. The results are set out in Table 4.

TABLE 4

| Example No. | Al:Ti (atomic ratio) | Cl:Ti (atomic ratio) | Ether:TiCl₃ (molar ratio) (a) | P:Ti (atomic ratio) (b) | Surface Area (m²/g) | X-ray data |
|---|---|---|---|---|---|---|
| 1 | 0.288 | 3.59 | | | 2.9 | |
| 2 | 0.104 | 3.25 | 0.089 | 0.57 | 2.0 | |
| 3 | 0.118 | 3.15 | 0.108 | 0.02 | | β-form plus layer structure |
| 4 | 0.116 | 3.28 | 0.072 | 0.095 | | β-form only |
| 5 | 0.127 | 3.33 | 0.10 | 0.051 | 1.1 | |
| 6 | 0.109 | 3.19 | 0.058 | 0.044 | | |
| 7 | 0.135 | 3.13 | 0.005 | 0.055 | 6.4 | β-form plus layer structure |
| 11 | 0.078 | 3.17 | | 0.7 | | β-form only |
| 12 | 0.089 | 3.20 | | | 1.1 | |
| 13 | 0.145 | 3.24 | | | 5.8 | β-form plus layer structure |
| 14 | 0.20 | 3.36 | | | 6.4 | β-form plus layer structure |
| 15 | 0.083 | 3.06 | | | 3.0 | |

Notes to Table 4
(a) Deduced from ether analysis on solutions of the product decomposed in methanol.
(b) Deduced from phosphorus analysis on solutions of the product decomposed in methanol.

EXAMPLES 16 to 30

Polymerisations were carried out in a 20 gallon (91 liter) stainless steel autoclave.

64 liters of an aliphatic hydrocarbon diluent (as used in Examples 5 to 7 and Comparative Example B) were charged into the vessel, and degassed at 60° C. for 30 minutes at a pressure of 50 millimeters of mercury. Propylene containing 0.15% by volume of hydrogen, was then admitted to the vessel in an amount to give a pressure of 1 psi (6.9 kN/m²) gauge. The diluent was stirred and stirring was continued throughout the following procedures. 0.536 mole of diethyl aluminium chloride, as a 25% by weight solution in the hydrocarbon diluent, was then added to the autoclave followed by 1 liter of the hydrocarbon diluent. 0.134 mole of titanium trichloride (prepared as described in Examples 1 to 15 or Comparative Examples A or B) was added as a suspension of titanium trichloride in the hydrocarbon diluent. 2 liters of the hydrocarbon diluent were then added.

The autoclave was maintained at 60° C. while propylene was passed into the autoclave at a constant rate of 22 pounds per hour (about 10 kilograms per hour). The propylene charge contained 0.15% by volume of hydrogen. A total of 33.5 kilograms of propylene were passed into the autoclave, after which the propylene feed was terminated and the autoclave pressure was allowed to run down to 5 psi (34.5 kN/m²) gauge. The residual propylene was then vented off and the polymer suspension passed into a glass-lined vessel. The autoclave was washed with 20 liters of the diluent which was also added to the glass-lined vessel. The contents of the glass-lined vessel were mixed with isopropanol in an amount of 2% by volume relative to the diluent. The mixture was stirred for 1 hour at 70° C., a mixture of isopropanol and water (containing 10% by volume of water) was added in an amount of 0.6% by volume relative to the diluent and stirring at 70° C. was continued for a further 2 hours.

The polymer suspension was then run into a further vessel containing 40 liters of demineralised water at ambient temperature, and the mixture was stirred for 30 minutes. The aqueous phase was then decanted off and a further 40 liters of demineralised water at ambient temperature were added and the process was repeated. The diluent was then filtered off and the polymer was dried at 100° C. in the fluidised bed using nitrogen as fluidising gas.

The results obtained, which include information on the properties of the polymer formed, are set out in Table 5.

TABLE 5

| Example or Comparative Example | Form of TiCl₃ (c) | Yield of soluble polymer (% by wt) | | Packing Density (g/l) | MFI | Flexural Modulus (GN/m²) | Activity |
|---|---|---|---|---|---|---|---|
| | | Diluent (d) | Residual (e) | (f) | (g) | (h) | (i) |
| 16 | 1 | 0.8* | | | | | |
| | | 1.3 | 3.2 | 417 | 18 | 1.56 | 22.2 |
| C | A | 5.3* | | | | | |
| | | 6.1 | 6.4 | 294 | 27 | 1.33 | 23.5 |
| 17 | 2 | 1.7* | | | | | |
| | | 2.4 | 4.6 | 506 | 13.5 | 1.63 | 21.7 |
| 18 | 3 | 2.6* | | | | | |
| | | 3.7 | 4.0 | 503 | 18 | 1.48 | 21.2 |
| 19 | 4 | 1.3* | | | | | |
| | | 1.7 | 5.3 | 506 | 7 | 1.63 | 13.9 |
| 20 | 5 | 1.5* | | | | | |
| | | 2.8 | 4.3 | 513 | 10 | 1.49 | 16.5 |
| 21 | 6 | 1.1* | | | | | |
| | | 1.8 | 1.3 | 500 | 8 | 1.50 | 16.0 |
| 22 | 7 | 0.7* | | | | | |
| | | 0.8 | 0.8 | 525 | 6 | 1.56 | 3.7 |
| D | B | 5.2* | | | | | |
| | | 6.9 | 3.9 | 494 | 17 | 1.33 | 20.4 |
| 23 | 8 | 2.8* | | | | | |
| | | 3.2 | 1.9 | 500 | 9 | 1.48 | 15.2 |
| 24 | 9 | 3.4* | | | | | |
| | | 4.4 | 2.4 | 500 | 8 | 1.59 | 16.4 |
| 25 | 10 | 2.1* | | | | | |
| | | 2.6 | 2.5 | 513 | 10.5 | 1.53 | 15.1 |
| 26 | 11 | 1.3* | | | | | |
| | | 2.3 | 3.6 | 500 | 13 | 1.48 | 18.0 |
| 27 | 12 | 1.6* | | | | | |
| | | 2.8 | 4.1 | 443 | 14 | 1.51 | 13.8 |
| 28 | 13 | 1.8* | | | | | |
| | | 3.4 | 2.1 | 506 | 10.9 | 1.57 | 21.1 |
| 29 | 14 | 4.4* | | | | | |
| | | 4.9 | 2.0 | 500 | 6 | 1.54 | 10.2 |
| 30 | 15 | 0.9* | | | | | |
| | | 1.6 | 3.7 | 513 | 16 | 1.53 | 18.7 |

TABLE 5-continued

| Example or Comparative Example | Form of TiCl₃ (c) | Yield of soluble polymer (% by wt) | | Packing Density (g/l) (f) | MFI (g) | Flexural Modulus (GN/m²) (h) | Activity (i) |
|---|---|---|---|---|---|---|---|
| | | Diluent (d) | Residual (e) | | | | |

Notes to Table 5
(c) Product of Examples 1 to 15 or Comparative Examples A or B respectively.
(d) Determined at the end of the polymerisation after adding the isopropanol.
*Determined by taking an aliquot portion of the polymerisation diluent at the end of the polymerisation before adding the isopropanol.
(e) Determined by dissolving 1 gramme of solid polymer in 50 ml of the same hydrocarbon diluent as is used for the polymerisation, by heating at 185° C. The solution is cooled to 60° C. and stirred at this temperature for 18 hours. The precipitated polymer is separated by filtration at 60° C., and the proportion of polymer which remains dissolved in the diluent at 60° C. is determined, by heating the solution to dryness.
(f) Determined by introducing 10 grammes of the polymer powder into a 50 ml flat-bottomed graduated tube of 2 cm internal diameter. The powder was compacted by striking the base of the tube against a horizontal surface a total of 30 times. The volume occupied by the polymer powder was then determined. Duplicate measurements were made.
(g) The melt flow index (MFI) was measured by ASTM Test Method D 1238-70, Condition N (190° C. and 10 kg).
(h) The flexural modulus was measured using a cantilever beam apparatus as described in Polymer Age, March 1970, pages 57 and 58. The deformation of a test strip at 1% skin strain after 60 seconds at 23° C. and 50% relative humidity was measured. The test strip, which had dimensions of approximately 150 × 19 × 1.6 mm, was prepared by mixing 23 g of the polymer with 0.1% by weight of an anti-oxidant ('Topanol' CA), and adding the mixture to a Brabender Plasticiser, at 190° C., 30 rpm and under a load of 10 kg to convert it to a crepe. The crepe was placed within a template, between aluminium foil and pressed by means of an electric Tangye press at a temperature of 250° C. The pressing was pre-heated for a period of 6 minutes, under just enough pressure to make the polymer flow across the template, that is an applied force of about 1 tonne. After the pre-heat period, the applied force was raised to 15.24 tonnes in 5.08 tonne increments, degassing (that is releasing pressure) every 5.08 tonnes. After 2 minutes at 15.24 tonnes, the press was cooled by means of air and water for 10 minutes or until room temperature was reached. The plaque obtained was then cut into strips of dimensions 150 × 19 × 1.6 mm. Duplicate strips of each polymer were placed into an annealing oven at 130° C. and after 2 hours at this temperature the heat was switched off and the oven cooled to ambient temperature at 15° C. per hour.
(i) Calculated from the weight of monomer fed per millimole of TiCl₃ in the catalyst during the final hour of the polymerisation for each atmosphere pressure of propylene. The propylene pressure is determined by correcting the total pressure for the presence of inert materials such as nitrogen and propane which are determined by titrating the gas space at the end of the polymerisation with bromine water.

EXAMPLE 31

The product of Example 2 was used to prepare a copolymer of propylene with ethylene.

Polymerisation was effected in a 20 gallon (91 liter) stainless steel autoclave. 64 liters of the hydrocarbon diluent (as used in Examples 16 to 30) were charged into the vessel and degassed at 60° C. for 30 minutes at a pressure of 50 mm Hg. Propylene containing 0.145% by volume of hydrogen was then admitted to the vessel at a rate of 22 lbs/hour in an amount to give a pressure of 1 psi (6.9 kN/m²) gauge. A vent on the vessel was opened and the propylene/hydrogen addition was continued for a further 5 minutes, the pressure in the autoclave being maintained at 1 psi (6.9 kN/m²) gauge throughout. The vent was then closed and the addition of the propylene/hydrogen mixture stopped. The contents of the vessel were stirred throughout the following procedures. 0.536 mole of diethyl aluminium chloride, as a 25% by weight solution in the hydrocarbon diluent, was added to the autoclave, followed by 1 liter of the hydrocarbon diluent. 0.134 mole of the product of Example 2 was added as a suspension of the titanium trichloride in the hydrocarbon diluent. This was washed in with a further 1 liter of hydrocarbon diluent.

The autoclave temperature was maintained at 60° C. whilst a total of 55.3 lbs (25.1 kg) of propylene containing 0.145% by volume of hydrogen was passed into the autoclave at a constant rate of 22 lbs/hour (about 10 kg/hour), after which the propylene/hydrogen feed was terminated and the autoclave pressure was allowed to run down to 18 psi (124 kN/m²) gauge, (equivalent to 30 psi (207 kN/m²) absolute of propylene), the excess pressure being due to the presence of inert materials. A total of 4.4 kg of ethylene was then metered into the autoclave at a feed rate of 2.3 kg/hour for 20 minutes, then 4.0 kgm/hour for 56 minutes. The ethylene feed was then terminated and the autoclave pressure allowed to run down to a total pressure of 2 psi (13.8 kN/m²) gauge.

The polymer suspension was passed into a 20 gallon (91 liter) glass-lined vessel. The autoclave was washed with 20 liters of the hydrocarbon diluent which was also added to the glass-lined vessel. The contents of the glass-lined vessel were mixed with isopropanol in an amount of 3% by volume relative to the diluent. The mixture was stirred for ½ hour at 70° C., and a mixture of isopropanol and distilled water (containing 10% by volume of water) was added in an amount of 0.6% by volume relative to the diluent and stirring at 70° C. continued for a further 1½ hours.

The polymer suspension was run into a further 20 gallon vessel containing 40 liters of demineralised water at ambient temperature and the mixture was stirred for 30 minutes. The stirrer was then stopped and the aqueous phase decanted off. A further 40 liters of demineralised water was added, stirring restarted and the process repeated. The diluent was then filtered off and the polymer was dried at 100° C. in a fluidised bed using nitrogen as the fluidising gas.

The polymer obtained had the properties set out in Table 6.

TABLE 6

| Ethylene Content (% by wt) | Yield of Soluble Polymer (% by wt) | | Packing Density (g/l) (f) | MFI (g) | Flexural Modulus (GN/m²) (h) | Low Temp Brittle Point (°C.) (k) |
|---|---|---|---|---|---|---|
| | Diluent (d) (j) | Residual (e) | | | | |
| 14.5 | 1.2** | | | | | |
| | 4.1*** | | | | | |
| | 6.2 | 7.5 | 466 | 6 | 1.07 | −42 |

Notes to Table 6
(d) to (h) are as defined in Notes to Table 5.
(j) **Determined by taking an aliquot portion of the polymerisation diluent at the end of the propylene run-down, before adding the ethylene.
***Determined by taking an aliquot portion of the polymerisation diluent at the end of the ethylene run-down, before adding the isopropanol.
(k) The low temperature brittle point was determined using the technique of ASTM Test Method D 746 modified by using specimens and specimen holder as in ASTM Bulletin No. 231, July 1958. The specimens were cut from a plaque prepared in the same manner as that from which were cut the test strips used in the flexural modulus test (Note (h) to Table 5).

EXAMPLE 32

The procedure of Example 2 was repeated with the exception that the n-heptane was replaced by a hydrocarbon fraction consisting mainly of C₇ isomers and having a boiling point range of 97° C. to 103° C. (this material will hereafter be referred to as "diluent 7").

EXAMPLE 33

Titanium tetrachloride was reduced with ethyl aluminium sesquichloride using the procedure of Example 1 with the exception that the n-heptane was replaced by diluent 7. At the end of the addition of the sesquichloride solution, the mixture was stirred for a further 4 hours whilst maintaining a temperature of 8° C. to 10° C.

A sample containing about 1 mole of titanium trichloride was separated from the reaction mixture and the suspension was diluted by the addition of an equal volume of a mixed aliphatic hydrocarbon fraction consisting predominantly of $C_{12}$ isomers. The mixture was then heated at 102° C. and maintained at that temperature for 90 minutes. The supernatant liquid was decanted off and the solid was then washed five times with 700 ml of the mixed aliphatic hydrocarbon fraction. The washed product was then suspended in 700 ml of the aliphatic hydrocarbon fraction.

The product was then treated with di-n-butyl ether and tributyl phosphine as described in Example 2 with the exception that the mixed aliphatic hydrocarbon fraction was used for all stages except the final washes which were effected using diluent 7, the temperature used was 110° C. and 0.112 mole of tributyl phosphine was used.

The final product was suspended in 700 ml of the mixed aliphatic hydrocarbon fraction.

EXAMPLE 34

The procedure of Example 2 was repeated with a number of variations as follows:

All stages of the procedure were carried out using the mixed aliphatic hydrocarbon fraction.

Reduction was effected by adding a 25% by weight solution of diethyl aluminium chloride, in an amount sufficient to provide 2.8 moles of the diethyl aluminium chloride, to 4 moles of titanium tetrachloride.

The reduced product was initially heated at 110° C.

The treatment with di-n-butyl ether and tributyl phosphine was effected at 120° C. and 0.112 mole of tributyl phosphine was used.

The product obtained was finally suspended in the mixed aliphatic hydrocarbon fraction to give a titanium trichloride concentration of 0.9 mole per liter of suspension.

EXAMPLES 35 to 37

The procedure of Example 2 was repeated with the exception that the n-heptane was replaced by the mixed aliphatic hydrocarbon fraction, the reduced and heated product was split into three portions for the treatment with the ether and phosphine, variations in this latter treatment being indicated in Table 7.

TABLE 7

| Example No. | Temperature of contacting with ether and phosphine (°C.) | Proportion of phosphine used (moles/mole $TiCl_3$) |
| --- | --- | --- |
| 35 | 90 | 0.084 |
| 36 | 90 | 0.140 |
| 37 | 100 | 0.084 |

EXAMPLES 38 to 40

(A) Reduction of titanium tetrachloride

A solution of 4.00 moles of titanium tetrachloride in 880 ml of the mixed aliphatic hydrocarbon fraction was placed in a 6.5 liter nitrogen-purged dry jacketed glass reaction vessel. The solution was maintained at a temperature of 25° C. and stirred at 250 rpm. A solution of ethyl aluminium sesquichloride in the mixed aliphatic hydrocarbon fraction (containing 0.85 mole of diethyl aluminium chloride for each liter of the solution) was added to the contents of the reaction vessel over a period of 4 hours. The quantity added was sufficient to provide 2.0 moles of the ethyl aluminium sesquichloride (this contained 2.0 moles of diethyl aluminium chloride). The temperature was maintained at 25° C. throughout the addition and the mixture was stirred. At the end of the addition of the sesquichloride solution, the mixture was stirred for a further 1 hour whilst maintaining the temperature of 25° C.

The whole mixture was then heated up to a temperature of 90° C. whilst still stirring. The temperature was maintained at 90° C. for 90 minutes, the mixture was allowed to cool and settle, the supernatant liquid was decanted off and the residual solid was then washed five times using 3 liters of the mixed aliphatic hydrocarbon fraction for each wash. The washed product was then suspended in 3 liters of the mixed aliphatic hydrocarbon fraction and the suspension obtained was then split up into several portions.

(B) Treatment with di-n-butyl ether and tributyl phosphine

The procedure used was essentially as described in Example 2 with the exception that n-heptane was replaced by the mixed aliphatic hydrocarbon fraction and other changes were made which are indicated in Table 8.

TABLE 8

| Example No. | Temperature of contacting with ether and phosphine (°C.) | Order of Addition of ether and phosphine (1) | | Proportion of phosphine used (moles/mole $TiCl_3$) |
| --- | --- | --- | --- | --- |
| | | First | Second | |
| 38 | 90 | DBE | TBP | 0.11 |
| 39 | 120 | DBE | TBP | 0.11 |
| 40 | 120 | TBP | DBE | 0.11 |

Note to Table 8
(1) DBE is di-n-butyl ether
TBP is tributyl phosphine.

EXAMPLES 41 to 43

The procedure of Example 34 was repeated with the exception that the conditions of treatment with di-n-butyl ether and tributyl phosphine were varied. The changes are summarised in Table 9.

TABLE 9

| Example No. | Temperature of contacting with ether and phosphine (°C.) | Proportion of phosphine used (moles/mole $TiCl_3$) |
| --- | --- | --- |
| 41 | 110 | 0.112 |
| 42 | 100 | 0.112 |
| 43 | 100 | 0.140 |

EXAMPLE 44

The procedure of Example 34 was repeated with the exception that the treatment with di-n-butyl ether and tributyl phosphine was effected at 115° C. and 0.10 mole of tributyl phosphine was used.

EXAMPLES 45 to 49

(A) Reduction of titanium tetrachloride

A solution of 4.00 moles of titanium tetrachloride in 880 ml of the mixed aliphatic hydrocarbon fraction was placed in a 6.5 liter nitrogen-purged dry jacketed glass reaction vessel. The solution was cooled to a temperature of 0° C. and stirred at 250 rpm. A 25% by weight solution of diethyl aluminium chloride in the mixed aliphatic hydrocarbon fraction was added to the contents of the reaction vessel over a period of 8 hours. The quantity added was sufficient to provide 2.8 moles of the diethyl aluminium chloride. The temperature was maintained at 0° C. throughout the addition and the mixture was stirred. At the end of the addition of the diethyl aluminium chloride solution, the mixture was stirred for a further 2 hours whilst maintaining the temperature at 0° C.

The whole mixture was then heated up to a temperature of 100° C. whilst still stirring. The temperature was maintained at 100° C. for 90 minutes, the mixture was allowed to cool and settle, the supernatant liquid was decanted off and the residual solid was then washed twice using 3 liters of the mixed aliphatic hydrocarbon fraction for each wash. The washed product was then suspended in 3 liters of the mixed aliphatic hydrocarbon fraction and a one-sixth portion was separated.

EXAMPLE 45

The one-sixth portion separated in (A) was treated with di-n-butyl ether and tributyl phosphine in the manner described in Example 2 except that n-heptane was replaced by the mixed aliphatic hydrocarbon fraction, the temperature used was 120° C. and 0.10 mole of tributyl phosphine was used.

EXAMPLES 46 TO 49

(B) Treatment with di-n-butyl ether

The residual major portion from (A) was heated, with stirring, to 100° C. On attaining the temperature of 100° C., di-n-butyl ether was added in an amount of 1.1 moles of ether for each mole of titanium trichloride present and the mixture was stirred at 100° C. for 1 hour and was then separated into two portions equal to one-half and one-third of the washed product of (A).

EXAMPLES 46 AND 47

(C) Treatment with tributyl phosphine

To the one-third portion from (B), whilst still at 100° C., was added 0.10 mole of tributyl phosphine for each mole of titanium trichloride and heating was continued for a further 1 hour at 100° C. The mixture was then allowed to settle and cool and was then washed twice with 1 liter of the mixed aliphatic hydrocarbon fraction, suspended in 1 liter of the mixed aliphatic hydrocarbon fraction and split into two equal portions.

EXAMPLE 46

One of the portions from (C) was washed twice more with 500 ml of the mixed aliphatic hydrocarbon fraction and finally suspended in 500 ml of the mixed aliphatic hydrocarbon fraction.

EXAMPLE 47

The other portion from (C) was heated again, with stirring, to 100° C., 0.10 mole of tributyl phosphine for each mole of titanium trichloride was added once a temperature of 100° C. had been attained and the temperature of 100° C. was maintained for 1 hour. The mixture was then allowed to settle and cool, washed four times with 500 ml of the mixed aliphatic hydrocarbon fraction and finally suspended in 500 ml of the mixed aliphatic hydrocarbon fraction.

EXAMPLES 48 AND 49

(D) Washing stage

The one-half portion from (B) was washed twice with 1.5 liters of the mixed aliphatic hydrocarbon fraction and suspended in 1.5 liters of the mixed aliphatic hydrocarbon fraction. A one-third portion was then separated.

EXAMPLE 48

The one-third portion from (D) was heated, with stirring, to 100° C., 0.10 mole of tributyl phosphine for each mole of titanium trichloride was added on attaining 100° C., and the temperature of the mixture was maintained at 100° C. for 1 hour. The mixture was then allowed to settle and cool, washed four times with 500 ml of the mixed aliphatic hydrocarbon fraction and finally suspended in 500 ml of the mixed aliphatic hydrocrbon fraction.

EXAMPLE 49

The residual portion from (D) was heated, with stirring, to 100° C., 1.1 moles of di-n-butyl ether, for each mole of titanium trichloride, were added on attaining 100° C. and the temperature was maintained at 100° C. for 1 hour.

After 1 hour at 100° C., the suspension was separated into two equal portions.

One portion (Comparative Example E) was allowed to settle and was washed four times with 500 ml of the mixed aliphatic hydrocarbon fraction and then suspended in 500 ml of the mixed aliphatic hydrocarbon fraction.

To the other portion, whilst still at 100° C., was added 0.10 mole of tributyl phosphine for each mole of titanium trichloride, the mixture was stirred for 1 hour at 100° C., allowed to settle and washed four times with 500 ml of the mixed aliphatic hydrocarbon fraction and then suspended in 500 ml of the mixed aliphatic hydrocarbon fraction.

EXAMPLE 50

The reduction procedure described as stage (A) of Examples 45 to 49 was repeated with the exception that the diethyl aluminium chloride was replaced by ethyl aluminium sesquichloride in an amount sufficient to provide the same proportion of diethyl aluminium chloride.

After holding at 0° C. for 2 hours, the whole mixture was heated to 120° C. and maintained at that temperature for 90 minutes. The mixture was then cooled and washed as in stage (A) of Examples 45 to 49 and the whole mixture was treated with di-n-butyl ether and tributyl phosphine as described in Example 2 with the exception that n-heptane was replaced by the mixed aliphatic hydrocarbon fraction, the temperature was 120° C. and 0.10 mole of tributyl phosphine was used for each mole of titanium trichloride. The final product was washed seven times.

EXAMPLE 51

The procedure of Example 50 was repeated with the exception that the initial heating was up to a temperature of 100° C., the treatment with the ether and the phosphine was effected at 115° C. and the final product was washed five times.

EXAMPLE 52

The reduction was effected in the manner described for stage (A) of Examples 45 to 49. The reduced product was heated at 110° C. for 90 minutes and the procedure was then as described for Example 51 with the exception that a temperature of 110° C. was used.

EXAMPLES 53 TO 64

Several of the products of Examples 32 to 52 were used to polymerise propylene using the procedure of Example 16 to 30. The results obtained are set out in Table 10.

TABLE 10

| Example (m) (n) (p) | Form of TiCl$_3$ (q) | Yield of soluble polymer (% by wt) Diluent (d) | Residual (e) | Packing Density (g/l) (f) | MFI (g) | Flexural Modulus (GN/m$^2$) (h) | Activity (i) |
|---|---|---|---|---|---|---|---|
| 53* | 34 | 1.13 | 1.89 | 533 | 11.3 | 1.62 | 4.7 |
| 54+ | 34 | 0.83 | 0.95 | 541 | 18.4 | 1.66 | 3.7 |
| 55 | 35 | 3.12 | 4.09 | 485 | 12.2 | 1.58 | 18.5 |
| 56** | 35 | 1.89 | 6.35 | 519 | 12.9 | 1.49 | 11.5 |
| 57* | 35 | 8.17 | 4.49 | 513 | 15.1 | 1.52 | 19.7 |
| 58 | 36 | 2.35 | 4.55 | 506 | 6.1 | 1.64 | 16.5 |
| 59* | 36 | 5.81 | 3.63 | 519 | 15.0 | 1.58 | 17.3 |
| 60 | 37 | 2.53 | 4.17 | 506 | 10.3 | 1.64 | 18.3 |
| 61* | 37 | 5.56 | 3.02 | 525 | 18.5 | 1.56 | 19.8 |
| 62 | 38 | 1.42 | 4.55 | 494 | 8.8 | 1.52 | 10.6 |
| 63 | 39 | 1.90 | 2.18 | 377 | 5.4 | 1.58 | 6.0 |
| 64++ | 40 | 2.31 | 1.78 | 455 | 5.4 | 1.69 | 3.3 |

Notes to Table 10
Notes (d) to (i) are as defined in Notes to Table 5.
(m)* Polymerisation effected at 70° C.
(n)+ Catalyst system contained 0.603 mole of diethyl aluminum chloride and 0.402 mole of titanium trichloride (molar ratio 9:6).
++ Catalyst system contained 0.536 mole of diethyl aluminium chloride and 0.268 mole of titanium trichloride (molar ratio 8:4).
(p)** The catalyst was pretreated by adding diethyl aluminium chloride (0.536 mole) and titanium trichloride (0.134 mole) to the polymerisation vessel, under a nitrogen atmosphere, and stirring these together for one hour at 30° C. before raising the temperature to 60° C. and introducing the propylene.
(q) Product of Examples 34 to 40.

EXAMPLES 65 TO 67

The products of Examples 38, 39 and 44 were used to prepare a copolymer of propylene with ethylene using the procedure of Example 31. The results obtained are set out in Table 11.

TABLE 11

| Example (n) (p) | Form of TiCl$_3$ (q) | Ethylene Content (% by wt) | Yield of Soluble Polymer (% by wt) Diluent (d) | Residual (e) | Packing Density (g/l) (f) | MFI (g) | Flexural Modulus (GN/m$^2$) (h) | Low Temp Brittle Point (°C.) (k) |
|---|---|---|---|---|---|---|---|---|
| 65**++ | 38 | 12.5 | 4.7 | 10.3 | 500 | 15.2 | 1.17 | −39 |
| 66**++ | 39 | 10.4 | 8.2 | 8.1 | 370 | 9.4 | 1.23 | −42 |
| 67++ | 44 | 12.4 | 4.5 | 9.9 | 525 | 8.7 | 1.21 | −40 |

Notes to Table 11
Notes (d) to (h) are as defined in Notes to Table 5.
Note (k) is as defined in Notes to Table 6.
Notes (n) to (q) are as defined in Notes to Table 10.

EXAMPLES 68 TO 80

Some of the products of Examples 32 to 52 were used to prepare a copolymer of propylene and ethylene.

Polymerisation was effected in a 20 gallon (91 l) stainless steel autoclave. 64 liters of the hydrocarbon diluent (as used in Examples 16 to 30) were charged into the vessel and degassed at 60° C. for 30 minutes at a pressure of 50 mm Hg. Propylene containing 0.175% by volume of hydrogen was then admitted to the vessel at a rate of 22 lbs/hr in an amount to give a pressure of 1 psi (6.9 kN/m$^2$) gauge. A vent on the vessel was opened and the propylene/hydrogen addition was continued for a further 5 minutes, the pressure in the autoclave being maintained at 1 psi (6.9 kN/m$^2$) gauge throughout. The vent was then closed and the addition of the propylene/hydrogen mixture stopped. The contents of the vessel were stirred throughout the following procedures. 0.536 mole of diethyl aluminium chloride, as a 25% by weight solution in the hydrocarbon diluent, was added to the autoclave, followed by 1 liter of the hydrocarbon diluent. 0.134 mole of a titanium trichloride product of one of Examples 32 to 52 was added as a suspension in the hydrocarbon diluent. This was washed in with a further 1 liter of hydrocarbon diluent.

The autoclave temperature was maintained at 60° C. whilst a total of 60.3 lbs (27.4 kg) of propylene containing 0.175 volume % of hydrogen was passed into the autoclave at a constant rate of 22 lbs/hour (about 10 kg/hour), after which the propylene/hydrogen feed was terminated and the autoclave pressure was allowed to run down to 10 psi (69 kN/m$^2$) gauge, (equivalent to 20 psi (138 kN/m$^2$) absolute) of propylene, the excess pressure being due to the presence of inert materials. A total of 2.07 kg of ethylene was then metered into the autoclave at a feed rate of 2.3 kg/hour for 20 minutes, then 4.0 kgm/hour for 20 minutes. The ethylene feed was then terminated and the autoclave pressure allowed to run down to a total pressure of 2 psi (13.8 kN/m$^2$) gauge.

The polymer suspension was passed into a 20 gallon (91 l) glass-lined vessel. The autoclave was washed with 20 liters of the hydrocarbon diluent which was also added to the glass-lined vessel. The contents of the glass-lined vessel were mixed with isopropanol in an amount of 3% by volume relative to the diluent. The mixture was stirred for ½ hour at 70° C., and a mixture of isopropanol and distilled water (containing 10% by volume of water) was added in an amount of 0.6% by volume relative to the diluent and stirring at 70° C. continued for a further 1½ hours.

The polymer suspension was run into a further 20 gallon vessel containing 40 liters of demineralised water at ambient temperature and the mixture was stirred for 30 minutes. The stirrer was then stopped and the aqueous phase decanted off. A further 40 liters of demineralised water were added, stirring restarted and the process repeated. The diluent was then filtered off and the polymer was dried at 100° C. in a fluidised bed using nitrogen as the fluidising gas.

Further details of the process used and the properties of the polymers obtained are set out in Table 12.

TABLE 12

| Example or Comparative Example (n) (p) | Form of TiCl$_3$ (r) | Ethylene Content (% by wt) | Yield of Soluble Polymer (% by wt) | | Packing Density (g/l) (f) | MFI (g) | Flexural Modulus (GN/m$^2$) (h) | Low Temp Brittle Point (°C.) (k) | Activity (i) |
|---|---|---|---|---|---|---|---|---|---|
| | | | Diluent (d) | Residual (e) | | | | | |
| 68+ | 34 | 5.7 | 2.8 | 4.5 | 533 | 15.7 | 1.46 | −28 | 3.4 |
| 69 | 37 | 4.9 | 5.6 | 4.3 | 506 | 7.6 | 1.41 | −23 | 16.3 |
| 70**++ | 38 | 5.3 | 2.7 | 7.9 | 500 | 40.5 | 1.40 | −20 | 7.8 |
| 71**++ | 39 | 5.1 | 2.8 | 4.9 | 408 | 20.8 | 1.40 | −29 | 5.0 |
| 72++ | 44 | 5.4 | 3.5 | 7.4 | 525 | 16.5 | 1.29 | −17 | 8.5 |
| 73 | 45 | 5.5 | 1.7 | 6.1 | 533 | 7.4 | 1.39 | −28 | 3.6 |
| 74 | 46 | 6.1 | 3.2 | 7.3 | 509 | 12.7 | 1.31 | −21 | 14.6 |
| 75 | 47 | 5.4 | 2.9 | 8.1 | 525 | 6.8 | 1.37 | −28 | 7.95 |
| 76 | 48 | 5.4 | 4.7 | 10.8 | 500 | 11.2 | 1.35 | −26 | 14.5 |
| 77 | 49 | 5.9 | 4.5 | 9.7 | 500 | 11.9 | 1.40 | −34 | 15.9 |
| F | E | 5.4 | 9.8 | 9.2 | 488 | 33.7 | 1.27 | −10 | 23.1 |
| 78 | 50 | 5.8 | 3.3 | 7.5 | ND | 12.4 | 1.46 | −23 | 3.5 |
| 79 | 51 | 5.6 | 4.2 | 7.9 | ND | 10 | 1.46 | −25 | 6.0 |
| 80 | 52 | 4.4 | 4.2 | 5.6 | ND | 16.3 | 1.44 | −24 | 10 |

Notes to Table 12
Notes (d) to (i) are as defined in Notes to Table 5.
Note (k) is as defined in Notes to Table 6.
Notes (n) and (p) are as defined in Notes to Table 10.
(r) Product of Examples 34 to 52 and Comparative Example E.

EXAMPLE 81

A homopolymerisation process was carried out continuously in a series of 5 interconnected 5 gallon stainless steel autoclaves wherein the transfer lines between each adjacent pair of vessels were provided with isolation valves.

Into each of the second, third, fourth and fifth autoclaves was placed a sample of a live polymer suspension (that is one in which there had been no treatment to deactivate the catalyst) which had been prepared by a technique as described in Examples 16 to 30 but omitting the treatment with isopropanol, and subsequent treatments. The contents of these vessels were stirred, the vessels were maintained at 60° C. and the isolation valves were kept closed.

A separate homopolymerisation was effected in the first vessel at 60° C. by adding propylene gas containing 0.26% by volume of hydrogen, at a rate sufficient to maintain the autoclave pressure at 35 psi (241 kN/m$^2$) gauge into 15 liters of stirred, degassed hydrocarbon diluent containing 0.14 mole diethyl aluminium chloride and 0.07 mole of the titanium trichloride product of Example 41.

When a polymer concentration of 200 g of polymer per liter of diluent had been attained in the first autoclave, continuous polymerisation was initiated by opening the isolation valves in the transfer lines between each pair of autoclaves. The feeds to the vessels were as follows:

First vessel - 7 liters per hour of the hydrocarbon diluent; 2 liters per hour of a catalyst mixture containing 0.018 mole of titanium trichloride per liter of diluent and 0.036 mole of diethyl aluminium chloride per liter of diluent; and sufficient of the propylene/0.26% by volume of hydrogen mixture to maintain a pressure of 35 psi (241 kN/m$^2$) gauge in this vessel.

Second vessel - The propylene/hydrogen mixture was also added to this vessel. The relative rates of feed of the propylene/hydrogen mixture to the first and second vessels were controlled in dependence on the liquid level of the suspension in each vessel to maintain the levels in each vessel at between 22 and 25 liters of suspension.

Third vessel - The propylene/hydrogen mixture was fed to this vessel in an amount equivalent to 21.5% of the total quantity of propylene feed to all the vessels.

Fourth and Fifth vessels - No additions were made to these vessels, other than the polymer suspensions transferred from the preceding vessel in the series.

The suspension of homopolymer formed in the fifth vessel was passed from this vessel into a continuous cascade deashing system, which provided a similar treatment to that described in Examples 16 to 30. The rate of removal of the homopolymer suspension from the fifth vessel was controlled to maintain equilibrium levells within the system.

Homopolymerisation was effected continuously for 30 hours.

The polymer obtained had the following characteristics:

| | |
|---|---|
| Diluent Soluble Polymer (d) | 1.4% by wt |
| Residual Soluble Polymer (e) | 2.2% by wt |
| Packing density (f) | 556 g/l |
| MFI (g) | 15.8 |
| Flexural Modulus (h) | 1.60 GN/m$^2$ |

(d) to (h) are as defined in Notes to Table 5.

EXAMPLE 82

A copolymerisation process was carried out continuously in the apparatus described in Example 81.

Into each of the second, third, fourth and fifth autoclaves was placed a sample of a live polymer suspension (that is one in which there had been no treatment to deactivate the catalyst) which had been prepared by a technique as described in Examples 16 to 30 but omitting the treatment with isopropanol, and subsequent treatments. The contents of these vessels were stirred, the vessels were maintained at 60° C. and the isolation valves were kept closed.

A separate homopolymerisation was effected in the first vessel at 60° C. by adding propylene gas containing 0.32% by volume of hydrogen, at a rate sufficient to maintain the autoclave pressure at 35 psi (241 kN/m$^2$) gauge into 15 liters of stirred, degassed hydrocarbon diluent containing 0.12 mole diethyl aluminium chloride and 0.06 mole of the titanium trichloride product of Example 41.

When a polymer concentration of 200 g of polymer per liter of diluent had been attained in the first autoclave, continuous polymerisation was initiated by opening the isolation valves in the transfer lines between each pair of autoclaves. The feeds to the vessels were as follows:

First vessel - 7 liters per hour of the hydrocarbon diluent; 2 liters per hour of a catalyst mixture containing 0.018 mole of titanium trichloride per liter of diluent and 0.036 mole of diethyl aluminium chloride per liter of diluent; and sufficient of the propylene/0.32% by volume of hydrogen mixture to maintain a pressure of 35 psi (241 kN/m$^2$) gauge in this vessel.

Second vessel - The propylene/hydrogen mixture was also added to this vessel. The relative rates of feed of the propylene/hydrogen mixture to the first and second vessels were controlled in dependence on the liquid level of the suspension in each vessel to maintain the levels in each vessel at between 22 and 25 liters of suspension.

Third and Fourth vessels - No additions were made to these vessels, other than the polymer suspension transferred from the preceding vessel in the series.

Fifth vessel - Ethylene and the propylene/hydrogen mixture were separately fed into this vessel. The amount of ethylene was continuously monitored and controlled to be 7.4% by weight of the total monomer being fed to the whole system. The amount of the propylene/hydrogen mixture was also controlled such that the molar ratio of propylene to ethylene polymerised within the fifth vessel was 0.58:1.

The suspension of copolymer formed in the fifth vessel was passed from this vessel into a continuous cascade deashing system, which provided a similar treatment to that described in Examples 16 to 30. The rate of removal of the copolymer suspension from the fifth vessel was controlled to maintain equilibrium levels within the system.

Polymerisation was effected continuously for 40 hours.

The characteristics of the polymer obtained are as follows:

| | |
|---|---|
| Diluent Soluble Polymer (d) | 7.5% by wt |
| Residual Soluble Polymer (e) | 9.4% by wt |
| Packing density (f) | 370 g/l |
| MFI (g) | 17.6 |
| Flexural Modulus (h) | 1.41 GN/m$^2$ |
| Low temp Brittle Point (k) | −31° C. |

(d) to (h) are as defined in Notes to Table 5
(k) is as defined in Notes to Table 6.

EXAMPLES 83 TO 85

Titanium tetrachloride was reduced, heated to 100° C., cooled, washed and finally resuspended as described in stage (A) of Examples 45 to 49.

Portions of the product obtained were treated as generally described in Example 2 with the exception that the temperature was varied, different phosphorus compounds were used in varying proportions, the mixed aliphatic hydrocarbon fraction was used throughout (rather than n-heptane), and the heated product was washed only three times. Further details are set out in Table 13.

EXAMPLES 86 TO 88

The procedure of Examples 83 to 85 was repeated except that the titanium tetrachloride was reduced using a sufficient quantity of ethyl aluminium sesquichloride to provide 0.7 mole of diethyl aluminium chloride for each mole of titanium tetrachloride, other variations being as set out in Table 13.

TABLE 13

| | | Heat Treatment | | |
|---|---|---|---|---|
| | Reducing | | Phosphorus Compound | |
| Example No. | Agent (s) | Temp (°C.) | Type (t) | Amount (Mole/Mole TiCl$_3$) |
| 83 | DEAC | 110 | TBPO | 0.08 |
| 84 | DEAC | 110 | TPPO | 0.10 |
| 85 | DEAC | 100 | TPPO | 0.10 |
| 86 | EASC | 110 | TPPO | 0.10 |
| 87 | EASC | 120 | TPPO | 0.10 |
| 88 | EASC | 110 | TPPO | 0.15 |

Notes to Table 13
(s) DEAC is diethyl aluminium chloride
EASC is ethyl aluminium sesquichloride
(t) TBPO is tri-n-butyl phosphine oxide
TPPO is triphenyl phosphine oxide.

EXAMPLE 89

The procedure of Examples 83 to 85 was repeated with the exception that the titanium tetrachloride solution was more dilute (1 volume of titanium tetrachloride to 4 volumes of the mixed aliphatic hydrocarbon fraction), the temperature was 110° C., and 0.10 mole, for each mole of titanium trichloride, of triphenyl phosphine oxide was used.

EXAMPLES 90 TO 96

The polymerisation procedure described in Examples 68 to 80 was carried out using 0.536 mole of diethyl aluminium monochloride and 0.268 mole of a titanium trichloride product of one of Examples 83 to 89. The polymerisation results are summarised in Table 14.

TABLE 14

| Example | Form of TiCl$_3$ | Ethylene Content (% by wt) | Yield of Soluble Polymer (% by wt) | | Packing Density (g/l) (f) | MFI (g) | Flexural Modulus (GN/m$^2$) (h) | Low Temp Brittle Point (°C.) (k) | Activity (i) |
|---|---|---|---|---|---|---|---|---|---|
| | | | Diluent (d) | Residual (e) | | | | | |
| 90 | 83 | 5.9 | 3.5 | 7.8 | 506 | 30.1 | 1.45 | −28 | 13.9 |
| 91 | 84 | 5.5 | 4.9 | 5.0 | 475 | 25 | 1.43 | −23 | 11.5 |
| 92 | 85 | 4.9 | 7.1 | 3.1 | 465 | 24.2 | 1.48 | −18 | 12.0 |
| 93 | 86 | 5.6 | 5.1 | 6.6 | 525 | 33.1 | 1.38 | −18 | 12.7 |
| 94 | 87 | 5.6 | 5.2 | 5.7 | 500 | 15.5 | 1.46 | −27 | 4.0 |
| 95 | 88 | 5.3 | 5.8 | 7.0 | 519 | 28.8 | 1.53 | −17 | 13.4 |

TABLE 14-continued

| Example | Form of TiCl$_3$ | Ethylene Content (% by wt) | Yield of Soluble Polymer (% by wt) Diluent (d) | Yield of Soluble Polymer (% by wt) Residual (e) | Packing Density (g/l) (f) | MFI (g) | Flexural Modulus (GN/m$^2$) (h) | Low Temp Brittle Point (°C.) (k) | Activity (i) |
|---|---|---|---|---|---|---|---|---|---|
| 96 | 89 | 5.1 | 5.0 | 5.4 | 444 | 11.8 | 1.45 | −32 | 9.6 |

Notes to Table 14
Notes (d) to (i) are as defined in Notes to Table 5.
Note (k) is as defined in Notes to Table 6.

EXAMPLES 97 TO 99

The procedure was generally as described for Examples 83 to 85 with the exception that the temperature was 110° C. in all cases and 0.10 mole, for each mole of titanium trichloride, of various phosphorus compounds were used. The phosphorus compounds used are set out in Table 15.

TABLE 15

| Example | Phosphorus compound |
|---|---|
| 97 | Triethyl phosphate |
| 98 | Tri-n-butyl phosphite |
| 99 | Tri-n-butyl phosphate |

EXAMPLE 100

The procedure of Examples 97 to 99 was repeated except that the titanium tetrachloride solution consisted of 1 volume of titanium tetrachloride to 3 volumes of the mixed aliphatic hydrocarbon diluent and the phosphorus compound used was triphenyl phosphate.

EXAMPLE 101

The procedure of Examples 97 to 99 was repeated except that, after the initial heating to 100° C., the product was washed only once and, in the subsequent heating, the phosphorus compound used was triphenyl phosphine.

EXAMPLE 102

The procedure of Examples 97 to 99 was repeated with the exception that the initial heating to 100° C. was omitted (but the washing stage was retained), the ether was diphenyl ether (used as a mixture of 75% by weight of diphenyl ether and 25% by weight of diphenyl) and the phosphorus compound used was tributyl phosphine.

EXAMPLE 103

The procedure of Examples 97 to 99 was repeated with the exception that the ether was diphenyl ether (used as a mixture of 75% by weight of diphenyl ether and 25% by weight of diphenyl) and the phosphorus compound used was tributyl phosphine.

EXAMPLES 104 TO 110

The polymerisation procedure described in Examples 68 to 80 was carried out using 0.536 mole of diethyl aluminium chloride and 0.268 mole of a titanium trichloride product of one of Examples 97 to 103. The polymerisation results are summarised in Table 16.

TABLE 16

| Example (n) | Form of TiCl$_3$ | Ethylene Content (% by wt) | Yield of Soluble Polymer (% by wt) Diluent (d) | Yield of Soluble Polymer (% by wt) Residual (e) | Packing Density (g/l) (f) | MFI (g) | Flexural Modulus (GN/m$^2$) (h) | Low Temp Brittle Point (°C.) (k) | Activity (i) |
|---|---|---|---|---|---|---|---|---|---|
| 104 | 97 | ND | 5.0 | 8.3 | 519 | 23 | 1.31 | −18 | 15.4 |
| 105 | 98 | ND | 3.6 | 6.9 | 526 | 13 | 1.20 | −26 | 13.7 |
| 106 | 99 | 6.2 | 4.8 | 8.1 | 513 | 44 | 1.18 | −21 | 16.8 |
| 107 | 100 | ND | 6.0 | ND | 541 | 13.8 | 1.28 | −24 | 10.7 |
| 108+ | 101 | 5.9 | 3.3 | 7.0 | 526 | 8 | 1.42 | −31 | 2.2 |
| 109 | 102 | 6.1 | 5.4 | 9.6 | 519 | 23 | 1.22 | −23 | 4.8 |
| 110 | 103 | 5.4 | 7.7 | 11.0 | 460 | 28 | 1.23 | −33 | 3.8 |

Notes to Table 16
Notes (d) to (i) are as defined in Notes to Table 5
Note (k) is as defined in Notes to Table 6
Note (n) is as defined in Notes to Table 10.

EXAMPLES 111 TO 123

Several samples of a titanium trichloride reduction product were prepared using the procedure of stage A) of Examples 45 to 49.

The samples were each divided into a number of portions which were treated as generally described in Example 2 with the exception that the temperature was varied, different phosphorus compounds were used in varying proportions, the mixed aliphatic hydrocarbon fraction was used throughout (rather than n-heptane), and the heated product was washed only three times. Further details are set out in Table 17.

TABLE 17

| | Heat Treatment | | |
|---|---|---|---|
| | | Phosphorus Compound | |
| Example No. | Temp (°C.) | Type (t) (u) | Amount (Mole/Mole TiCl$_3$) |
| 111 | 110 | TEPAT | 0.15 |
| 112 | 110 | TPPAT | 0.10 |
| 113 | 120 | TEPAT | 0.10 |
| 114 | 100 | TPP | 0.15 |
| 115 | 110 | TPP | 0.05 |
| 116 | 110 | TPIT | 0.10 |
| 117 | 110 | TNPIT | 0.10 |
| 118 | 110 | TPPO | 0.15 |

TABLE 17-continued

| | Heat Treatment | | |
| Example No. | Temp (°C.) | Phosphorus Compound Type (t) (u) | Amount (Mole/Mole TiCl₃) |
| --- | --- | --- | --- |
| 119 | 120 | TPP | 0.02 |
| 120 | 120 | TNPIT | 0.10 |
| 121 | 110 | TOPO | 0.10 |
| 122 | 100 | TOPO | 0.10 |
| 123 | 110 | TOPO | 0.075 |

Notes to Table 17
Note (t) is as defined in Notes to Table 13
Note (u) TEPAT is triethyl phosphate
TPPAT is triphenyl phosphate
TPP is triphenyl phosphine
TPIT is triphenyl phosphite
TNPIT is tris(nonylphenyl)phosphite
TOPO is trioctyl phosphine oxide.

EXAMPLES 124 TO 138

The polymerisation procedure described in Examples 68 to 80 was carried out using a titanium trichloride product obtained as described in Examples 111 to 123. Except where otherwise indicated, 0.536 mole of diethyl aluminium chloride and 0.268 mole of titanium trichloride were used. The polymerisation results are summarised in Table 18.

TABLE 18

| Example (p) (v) | Form of TiCl₃ | Ethylene Content (% by wt) | Yield of Soluble Polymer (% by wt) Diluent (d) | Yield of Soluble Polymer (% by wt) Residual (e) | Packing Density (g/l) (f) | MFI (g) | Flexural Modulus (GN/m²) (h) | Low Temp Brittle Point (°C.) (k) | Activity (i) |
| --- | --- | --- | --- | --- | --- | --- | --- | --- | --- |
| 124 | 111 | 5.3 | 6.8 | 4.1 | 513 | 15.4 | 1.33 | −21 | 14.5 |
| 125 | 112 | 5.5 | 6.0 | 7.0 | 541 | 13.8 | 1.28 | −24 | 10.7 |
| 126 | 113 | 4.9 | 7.3 | 5.4 | 494 | 16.1 | 1.25 | −19 | 9.3 |
| 127 | 114 | 4.7 | 6.5 | 3.6 | 519 | 19.4 | 1.31 | −16 | 10.1 |
| 128 | 115 | 4.8 | 3.9 | 4.6 | 519 | 7.9 | 1.26 | −28 | 7.8 |
| 129 | 116 | 5.5 | 4.2 | 7.3 | 526 | 27.6 | 1.45 | −19 | 10.5 |
| 130 | 117 | 5.4 | 6.8 | 8.1 | 513 | 38.5 | 1.46 | −20 | 13.8 |
| 131**° | 116 | 5.2 | 4.5 | 9.0 | 556 | 22.7 | 1.39 | −26 | 5.9 |
| 132**° | 117 | 4.9 | 7.2 | 10.4 | 533 | 21.2 | 1.32 | −30 | 12.2 |
| 133 | 118 | 4.4 | 6.8 | 5.9 | 500 | 24.6 | 1.50 | −11 | 9.7 |
| 134 | 119 | 4.9 | 4.9 | 8.6 | 526 | 26.3 | 1.23 | −20 | 9.6 |
| 135 | 120 | 5.0 | 5.0 | 9.3 | 548 | 11.0 | 1.29 | −30 | 4.7 |
| 136° | 121 | ND | 6.8 | 10.8 | 506 | 27.4 | 1.49 | −22 | 14.7 |
| 137 | 122 | 5.4 | 7.3 | 6.4 | 506 | 29.0 | 1.34 | −15 | 19.3 |
| 138 | 123 | 4.9 | 4.6 | 7.1 | 529 | 19.0 | 1.23 | −14 | 16.1 |

Notes to Table 18
Notes (d) to (i) are as defined in Notes to Table 5
Note (k) is as defined in Notes to Table 6
Note (p) is as defined in Notes to Table 10
Note (v) °Catalyst system contained 0.536 mole of diethyl aluminium chloride and 0.134 mole of titanium trichloride (molar ratio 8:2).

EXAMPLES 139 TO 142

Titanium tetrachloride was reduced using the procedure described in stage (A) of Examples 45 to 49.

After holding at 0° C. for 2 hours, the whole mixture was then heated up to a temperature of 100° C. whilst still stirring. The temperature was maintained at 100° C. for one hour and then di-n-butyl ether was added in a quantity sufficient to provide 1.1 mole of the ether for each mole of titanium trichloride present in the suspension. Stirring at 100° C. was continued for a further hour, the mixture was allowed to cool and settle, the supernatant liquid was decanted off, and the residual solid was then washed three times using 3 liters of the mixed aliphatic hydrocarbon fraction for each wash. The washed product was then suspended in 3 liters of the mixed aliphatic hydrocarbon fraction.

Two one-third portions of the foregoing suspension were heated to 100° C., with stirring, a phosphorus compound was added on attaining 100° C. and stirring at 100° C. was continued for one hour. Each portion was then allowed to cool and was divided into two equal fractions. From one fraction of each portion the supernatant liquid was decanted, and the product was washed three times using 700 ml of the mixed aliphatic hydrocarbon fraction for each wash and was finally suspended in 700 ml of the mixed aliphatic hydrocarbon fraction. The other fraction of each portion was not washed.

Further details are set out in Table 19.

TABLE 19

| | Phosphorus compound used in second heat treatment | | |
| Example No. | Type (l) (u) | Amount (Mole/Mole TiCl₃) | Washing |
| --- | --- | --- | --- |
| 139 | TBP | 0.075 | YES |
| 140 | TBP | 0.075 | NO |
| 141 | TNPIT | 0.10 | YES |
| 142 | TNPIT | 0.10 | NO |

Notes to Table 19
Note (l) is as defined in Note to Table 8
Note (u) is as defined in Notes to Table 17.

EXAMPLES 143 TO 146

The polymerisation procedure described in Examples 68 to 80 was carried out using 0.536 mole of diethyl aluminium chloride and 0.268 mole of a titanium trichloride product of one of Examples 139 to 142, and different proportions of hydrogen in the propylene.

Further details, including the polymerisation results, are summarised in Table 20.

TABLE 20

| Example No. | Form of TiCl$_3$ | Amount H$_2$ (% mole relative to propylene) | Diluent Soluble Polymer (% wt) (d) | Packing Density (g/l) (f) | MFI (g) | Flexural Modulus (GN/m$^2$) (h) | Low Temp Brittle Point (°C.) (k) | Activity (i) |
|---|---|---|---|---|---|---|---|---|
| 143 | 139 | 0.25 | 5.2 | 540 | 7.0 | 1.32 | −28 | 7.5 |
| 144 | 140 | 0.25 | 4.9 | 520 | 9.5 | 1.40 | −26 | 8.1 |
| 145 | 141 | 0.21 | 5.9 | 500 | ND | 1.37 | −28 | 5.2 |
| 146 | 142 | 0.21 | 5.2 | 476 | ND | 1.47 | −31 | 4.8 |

Notes to Table 20
Notes (d) to (i) are as defined in Notes to Table 5
Note (k) is as defined in Notes to Table 6.

I claim:

1. A process for the production of a titanium trichloride-containing composition which process comprises
   (1) reducing titanium tetrachloride by reacting the titanium tetrachloride with a reducing agent under conditions to give a solid titanium trichloride product which includes an associated aluminium compound containing aluminium and chlorine atoms, wherein the titanium trichloride is formed predominantly in the beta-form;
   (2) contacting a suspension of the solid reduction product with compound E and compound L either simultaneously or sequentially, at least part of the contacting being effected while maintaining the suspension at a temperature of at least 60° C. in the presence of at least compound E or compound L; and
   (3) subsequent to the contacting with the compound E washing the solid product obtained with an inert hydrocarbon or inert halohydrocarbon liquid
   wherein
   E is an ether or a thioether;
   L is an organic phosphorus-containing Lewis Base compound of the general formula:

$$R^3R^4R^5P(O)_m$$

where
   R$^3$ is a hydrocarbyl, or a hydrocarbyloxy group wherein the hydrocarbyl group contains up to 18 carbon atoms;
   R$^4$ and R$^5$ which may be the same or different, are each a hydrogen atom or a gorup R$^3$; and
   m is 0 or 1.

2. The process of claim 1 wherein the product obtained is a composition of matter of the formula:

$$TiCl_3(AlR_xX_{3-x})_nE_aL_b$$

where
   R is a hydrocarbyl group;
   X is a halogen atom other than fluorine;
   E is an ether or a thioether;
   L is an organic phosphorus-containing Lewis Base compound;
   x is such that $0 \leq x \leq 3.0$;
   n is from 0 up to 0.5; and
   a and b are each, independently, from 0.001 up to 0.50.

3. The process of claim 1 wherein the reducing agent is an organic aluminium compound of the formula $$AlR_{x'}X_{3-x'} \text{ or } AlR_{x'}H_{3-x'}$$

and the reduction is effected in the essential absence of aromatic hydrocarbons,
   wherein
   R is a hydrocarbyl group;
   X is a halogen atom other than fluorine; and
   x' is such that $1.0 \leq x' \leq 3.0$.

4. The process of claim 3 wherein the group R is an alkyl group containing from 2 up to 10 carbon atoms, X is chlorine and the value of x' is such that $1.5 \leq x' \leq 2.0$.

5. The process of claim 1 wherein E is di-n-butyl ether, di-isoamyl ether or diphenyl ether.

6. The process of claim 1 wherein the compound L is tri-n-butyl phosphine, triphenyl phosphine, tri-n-butyl phosphine oxide, trioctyl phosphine oxide, triphenyl phosphine oxide, tributyl phosphite, triphenyl phosphite, tris(nonylphenyl)phosphite, triethyl phosphate, tributyl phosphate or triphenyl phosphate.

7. The process of claim 2 wherein, in the product obtained, the values of a and b are different, the value of a is from 0.01 up to 0.20 and the value of b is from 0.005 up to 0.20

8. The process of claim 1 wherein the product obtained has a specific surface area of from 1 up to 30 l m$^2$/g.

9. The process of claim 1 wherein the product obtained has an X-ray diffraction sprectrum which is that of the beta-form of titanium trichloride.

10. The process of claim 1 wherein the product of stage (1) is subjected to a thermal treatment at a temperature in the range from 40° C. up to 130° C. for a period of from 5 minutes up to 20 hours, and the thermally treated product is then subjected to stage (2) of the process.

11. The process of claim 1 wherein, in stage (2), the compound E and the compound L are added separately, the compound E is added first and is added as soon as the reduction product attains the temperature of at least 60° C.

12. The process of claim 1 wherein, in stage (2), the reduction product is contacted with compound E at the temperature of at least 60° C., the product is washed and the washed product is contacted with compound L at the temperature of at least 60° C.

13. The process of claim 1 wherein, in stage (2), the reduction product is heated to a temperature in the range from 90° C. up to 120° C., and the heating time is at least 2 hours and not more than 10 hours.

14. An olefine polymerisation catalyst comprising: (1) a titanium trichloride-containing material which is the product obtained by the process of claim 1; and (2) at least one organo-metallic compound of aluminium, or of a non-transition metal of Group IIA of the Periodic Table, or a complex of an organo-metallic compound of a non-transition metal of Group IA or Group IIA of the Periodic Table with an organo-aluminium compound.

15. The process of claim 1 wherein the reduction product of stage (1) remains in the solid phase throughout stages (2) and (3).

16. A process for the production of titanium trichloride-containing composition which process comprises
(1) reducing titanium tetrachloride by reacting the titanium tetrachloride with a reducing agent under conditions to give a titanium trichloride product which includes an associated aluminium compound containing aluminium and chlorine atoms, wherein the titanium trichloride is formed predominantly in the beta-form;
(2) contacting the reduction product with compound E and compound L either simultaneously or sequentially, at least part of the contacting being effected at a temperature of at least 60° C. in the presence of at least compound E or compound L by heating the reduction product to the temperature of at least 60° C. and then adding one, or both, of the compounds E and L to the heated material; and
(3) subsequent to the contacting with the compound E washing the product obtained with an inert hydrocarbon or inert halohydrocarbon liquid wherein
E is an ether or a thioether;
L is an organic phosphorus-containing Lewis Base compound of the general formula:

$$R^3R^4R^5P(O)_m$$

where
$R^3$ is a hydrocarbyl, or a hydrocarbyloxy group wherein the hydrocarbyl group contains up to 18 carbon atoms;
$R^4$ and $R^5$ which may be the same or different, are each a hydrogen atom or a group $R^3$; and
m is 0 or 1.

* * * * *